United States Patent [19]

Blewett et al.

[11] Patent Number: 4,469,912

[45] Date of Patent: Sep. 4, 1984

[54] PROCESS FOR CONVERTING α-OLEFIN DIMERS TO HIGHER MORE USEFUL OLIGOMERS

[75] Inventors: Charles W. Blewett, Fort Mitchell, Ky.; Stephen W. Turner, Hamilton, Ohio

[73] Assignee: National Distillers and Chemical Corporation, New York, N.Y.

[21] Appl. No.: 523,256

[22] Filed: Aug. 15, 1983

Related U.S. Application Data

[63] Continuation-in-part of Ser. No. 414,691, Sep. 3, 1982, abandoned.

[51] Int. Cl.$^3$ ............................ C07C 3/16; C07C 3/18
[52] U.S. Cl. ...................................... 585/525; 585/312; 585/324; 585/329; 585/510; 585/517; 585/519
[58] Field of Search ............... 585/312, 313, 324, 329, 585/510, 517, 525, 521, 518, 519, 832

[56] References Cited

U.S. PATENT DOCUMENTS

| | | | |
|---|---|---|---|
| 2,810,774 | 10/1957 | Serniuk | 585/525 |
| 2,816,944 | 12/1957 | Muessig et al. | 585/525 |
| 3,742,082 | 6/1973 | Brennan | 585/510 |
| 4,172,855 | 10/1979 | Shubkin et al. | 585/510 |
| 4,386,229 | 5/1983 | Heckelsberg et al. | 585/329 |

FOREIGN PATENT DOCUMENTS 1189985  6/1962  Fed. Rep. of Germany ...... 585/525

Primary Examiner—Delbert E. Gantz
Assistant Examiner—A. Pal
Attorney, Agent, or Firm—Tremain, Kenneth D.; Gerald A. Baracka

[57] ABSTRACT

A process is provided whereby the dimer fraction obtained from a boron trifluoride catalyzed oligomerization process is reacted with an α-olefin in the presence of a phosphoric acid-modified boron trifluoride catalyst to produce higher oligomeric products typically having viscosities (210° F.) in the 4 to 8 centistoke range.

7 Claims, No Drawings

PROCESS FOR CONVERTING α-OLEFIN DIMERS TO HIGHER MORE USEFUL OLIGOMERS

CROSS-REFERENCE TO RELATED APPLICATION

This is a continuation-in-part of copending application Ser. No. 414,691, filed Sept. 3, 1982, now abandoned.

BACKGROUND OF INVENTION

Synthetic hydrocarbon lubricants obtained from the Friedel-Crafts catalyzed oligomerization of α-olefins having from about 4 to 12 carbon atoms, particularly 1-octene and/or 1-decene, are known. For example, U.S. Pat. Nos. 3,149,178; 3,763,244 and 3,780,128 describe batch oligomerization processes for α-olefins, such as 1-decene, using boron trifluoride in combination with a promoter such as an alcohol or water. Also, continuous oligomerization processes utilizing boron trifluoride catalysts are described in U.S. Pat. Nos. 4,045,508 and 4,239,930.

Oligomer mixtures typically comprised of dimer, trimer, tetramer, pentamer and minor amounts of higher oligomers are obtained from such processes. Whereas the distribution of oligomers can be varied to some extent, depending on the reaction conditions, it is not possible to totally exclude the formation of the dimeric product with boron trifluoride catalyzed reactions. The dimer, being too volatile (low flash point) for most lubricating applications, is therefore separated from the higher oligomeric products by distillation. In some instances, the higher oligomers are further fractionated to obtain products having different viscosity specifications. The higher oligomeric products (consisting predominantly of trimer and tetramer) are then hydrogenated to improve the oxidative and thermal stability prior to formulation of the finished lubricant product.

In view of the substantial quantity of dimer (2 centistoke) product which is presently being produced in commercial α-olefin oligomerization processes and the limited number of formulations for which 2 centistoke fluids are employed, the supply far exceeds demand. It would be highly advantageous if a process were available whereby dimer produced in boron trifluoride catalyzed oligomerization processes could be readily and economically converted to higher and more useful oligomers. The dimer fraction obtained from such boron trifluoride catalyzed oligomerizations consists predominantly of highly branched internal olefins (trialkyl- and tetraalkyl-substituted olefins) and, due to the fact that the unsaturation is located within the molecule and sterically hindered, is relatively unreactive and generally considered to be unacceptable for recycling in the process for further reaction and conversion to higher oligomers.

U.S. Pat. No. 4,172,855 to Shubkin et al. discloses a two-stage process whereby an α-olefin is first reacted to obtain a product consisting mainly of dimers of said α-olefins. Ziegler-type catalysts, preferably alkyl aluminum compounds, are utilized in the first stage of the process since catalysts of this type maximize dimer formation. In contradistinction to the highly branched internal olefins obtained from BF$_3$ catalyzed oligomerizations, the dimers produced in the first stage of the Shubkin et al. process are primarily vinylidene-type

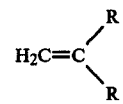

products which are highly reactive as a result of the terminal methylene moiety. Thus, in the second stage of the process, the Shubkin et al. dimers can be further reacted with a second α-olefin to obtain the more desirable higher oligomers. A Friedel-Crafts catalyst, preferably a promoted boron trifluoride catalyst, is utilized to catalyze the second stage reaction of the dimer and α-olefin. Promoters disclosed by Shubkin et al. for use with the BF$_3$ include water, alkanols, fatty acids, fatty acid esters, ethers and ketones.

SUMMARY OF THE INVENTION

We have now quite unexpectedly discovered a highly economical and efficient process whereby the highly branched unreactive dimers obtained from boron trifluoride catalyzed oligomerizations and which contain substantial amounts of trialkyl- and tetraalkyl-substituted olefinic products can be reacted with an α-olefin or α-olefin mixture to convert the dimer to more useful oligomeric products. Even more unexpectedly it has been discovered that acceptable dimer conversions are possible only using a promoted boron trifluoride catalyst wherein the promoter is a specific inorganic acid, namely phosphoric acid. Quite surprisingly, when catalysts promoted with the common organic promoters or other inorganic acids of comparable or higher pK$_a$ are employed, unacceptable dimer conversions are obtained. With the process of this invention, which utilizes a phosphoric acid-promoted boron trifluoride catalyst, it is possible to achieve conversions of dimer to higher oligomers in the range 55 to 60 percent while achieving acceptable reaction rates. It is also possible to vary the ratio of α-olefin to dimer in the process to obtain fluids having different viscosity specifications.

The process of this invention for converting dimers of α-olefins obtained from boron trifluoride catalyzed oligomerization processes to higher more useful oligomers comprises contacting the dimer with an α-olefin present in an amount ranging from 5:1 to 1:5 at a temperature from 5° C. to 75° C. and pressure from atmospheric up to 100 psi in the presence of 0.75 to 15 mole percent phosphoric acid-modified boron trifluoride catalyst. Useful dimers for the process are derived from C$_{6-12}$, and more preferably C$_{8-10}$, α-olefins. Similarly, the α-olefin reacted with the dimer can contain from 6 to 12 carbon atoms. The ratio of the dimer to α-olefin will preferably range from 3:1 to 1:3 with the catalyst present in an amount from 1 to 10 mole percent. Especially advantageous results are obtained at temperatures from 5° C. to 45° C. and pressures from atmospheric up to 10 psi.

DETAILED DESCRIPTION OF THE INVENTION

In accordance with this invention, it is now possible to effectively react the dimer product obtained from boron trifluoride catalyzed α-olefin oligomerization processes with an α-olefin or α-olefin mixture to efficiently produce higher oligomeric products.

The dimer used in the process of the invention is produced as a by-product in α-olefin oligomerization processes which utilize Friedel-Crafts catalysts, particularly boron trifluoride or promoted boron trifluoride catalysts. Most generally, when boron trifluoride is employed for such α-olefin oligomerization processes, it is utilized in conjunction with a promoter, typically an organic compound or water which complexes with the $BF_3$ to form a coordination complex having greater catalytic activity than the $BF_3$ by itself. Useful known organic promoters for this purpose include: aliphatic ethers, such as dimethyl ether, diethyl ether and the like; aliphatic alcohols such as methanol, ethanol, propanol, n-butanol, decanol, and the like; polyols, such as ethylene glycol; aliphatic carboxylic acids such as acetic acid, propanoic acid, and the like; esters, such as ethyl acetate, methyl propionate, and the like; ketones, such as acetone; aldehydes, such as acetaldehyde; and acid anhydrides, such as acetic anhydride, succinic anhydride, and the like.

Dimers employed for the process of this invention are typically derived from α-olefins having from 6 up to about 12 carbon atoms. More preferably, the dimer is obtained from the oligomerization of α-olefins having from 8 to 10 carbon atoms. The dimer is obtained from oligomerization procedures of the above types by fractional distillation to separate the dimer from trimer, tetramer and higher oligomers formed in the process. Typically the dimer product obtained by fractionation and used for the present process will contain less than about 5 percent by weight higher oligomers and consist predominantly of trialkyl- and tetraalkyl-substituted olefinic products having the respective formulae

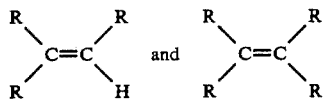

where R represents alkyl groups having the same or different number of carbon atoms, with the proviso that the total number of carbon atoms in the molecule falls within the limits prescribed above.

Reacted with the dimer is an α-olefin or mixture of α-olefins having from about 6 to 12 and, more preferably, 8 to 10 carbon atoms. While the weight ratio dimer to α-olefin can range from 5:1 to 1:5, it will most generally range from 3:1 to 1:3. The ratio used will be determined by the oligomer distribution desired and the reaction conditions. As will be evident to those skilled in the art, the distribution of oligomers will determine the viscosity of the final product. The α-olefin reacted with the dimer may be the same or different than the α-olefin from which the dimer is derived.

A phosphoric acid-modified boron trifluoride catalyst is employed for the process, however, as will be described more fully below, a portion of the $BF_3$ may be complexed with water. By the use of such catalysts, it is possible to achieve 55 percent or higher conversion of the dimer and acceptable reaction rates. Conversions of this magnitude and acceptable reaction rates are not possible using other modified $BF_3$ catalysts—even when the promoters are more strongly acidic than phosphoric acid.

The process can be carried out by mixing the dimer and α-olefin and adding the phosphoric acid/boron trifluoride catalyst thereto. It is more usual however, to charge the phosphoric acid, dimer and α-olefin to the reactor and then to introduce the boron trifluoride. The $BF_3$ can be introduced from a suitable pressure vessel containing the calculated amount of boron trifluoride. Sufficient $BF_3$ is added to completely complex with the phosphoric acid and any water which may be present. Alternatively, an excess of boron trifluoride may be added in which case the catalyst level is determined by the amount of phosphoric acid charged with the dimer and α-olefin. It has been found to be advantageous to maintain free boron trifluoride in the reaction medium. This is typically accomplished by introducing $BF_3$ subsurfacely throughout the course of the reaction. This latter procedure can be carried out at atmospheric pressure, or as is more generally the case, at a slight positive pressure.

The phosphoric acid employed using any of these procedures can be aqueous phosphoric acid, most generally containing 70 percent or more $H_3PO_4$, or orthophosphoric acid or polyphosphoric acid can be employed. When aqueous phosphoric acid is utilized, a portion of the $BF_3$ will be complexed with water. This is not detrimental to the process so long as the phosphoric acid constitutes 50 percent or more of the aqueous phosphoric acid solution.

The temperature required for reaction of the dimer and α-olefin can range from about 5° C. to 75° C. with temperatures in the range 5° C. to 45° C. being particularly advantageous. The pressure at which the process is carried out can be varied widely—from atmospheric up to about 100 psi. However, the pressure will most generally range from atmospheric up to about 10 psi.

The phosphoric acid-boron trifluoride catalyst is employed in an amount from about 0.75 to 15 mole percent (moles of phosphoric acid per mole of feed—dimer plus α-olefin). Preferably, from about 1 to 10 mole percent of the coordinated $BF_3$ catalyst is utilized. In those instances where an amount of $BF_3$ in excess of that required to coordinate with the phosphoric acid is employed, the catalyst level is controlled by the amount of phosphoric acid charged to the reactor.

The usual procedure for carrying out the process involves charging the dimer, α-olefin and phosphoric acid to a reaction vessel equipped with a thermometer, agitator and inlet tube for the subsurface addition of $BF_3$. The reactor is also equipped with an outlet tube connected to a trap containing aqueous sodium hydroxide solution. Excess $BF_3$ is vented to the trap for destruction. Heat is then applied while sparging the reaction mixture with nitrogen. When the desired temperature is reached, the nitrogen flow is stopped and gaseous $BF_3$ is introduced under a slight positive pressure (about 2 inches of water pressure). The temperature of the reaction is maintained by means of a temperature bath. When the desired conversion of dimer and/or α-olefin is achieved, the reactor is cooled and the reaction product washed with aqueous sodium hydroxide. The product is hydrogenated and distilled to obtain a product having the necessary oxidative and thermal stability and viscosity. If desired, the product may be distilled prior to hydrogenation.

It is possible to obtain useful lubricants having varying viscosity specifications by judicious selection of the process conditions and by fractionation of the product. Highly useful lubricants having 210° F. viscosities in the range 4 to 8 centistoke can be produced in this manner. Such products are utilized for a variety of known lubricant applications.

The products of this invention obtained by the reaction of dimer and α-olefins can be formulated using conventional additives. These products can be used as the sole basestock or can be blended with other synthetic or petroleum oils for the formulation of useful lubricant products.

The following examples illustrate the process of this invention more fully, however, they are not intended as a limitation on the scope thereof. All parts and percentages are on a weight basis unless otherwise indicated.

The dimer employed in all of the examples was obtained by fractionation of the product obtained from the oligomerization of 1-decene using an alcohol promoted boron trifluoride catalyst. After separation from the higher oligomers, the resulting dimer fraction contained 5 percent or less higher oligomers, primarily trimer, and had a viscosity (210°) in the range of 1.7–2.2 centistokes. The dimeric olefinic products were primarily trialkyl-substituted olefins and tetraalkyl-substituted olefins, which were present in a ratio of about 1:1.

EXAMPLE I

A glass reactor equipped with a stirrer, subsurface gas inlet and thermometer was charged with equal parts dimer and 1-decene. A solution of 70 percent aqueous phosphoric acid was added so that 1 mole percent phosphoric acid was present, based on the dimer/1-decene mixture. The temperature of the mixture was then lowered to 5° C. while stirring and sparging with nitrogen. The nitrogen flow was then stopped and gaseous boron trifluoride introduced at a rate sufficient to maintain a slight positive pressure within the reactor (2" of water pressure). Excess boron trifluoride was vented into a trap containing aqueous sodium hydroxide solution. The temperature of the reaction mixture was maintained at 5° C. After 4 hours 58.2 percent conversion of the dimer was obtained and the 1-decene was essentially completely reacted. The reaction was terminated by the addition of aqueous sodium hydroxide. After removal of unreacted dimer by fractionation, the resulting product consisted primarily of trimer, tetramer and pentamer (ratio 4.8:2.7:1) and a small amount of higher oligomers. This product had an average molecular weight of 502° and 210° F. viscosity of approximately 5.3 centistokes. Essentially equal proportions of 4 centistoke and 6 centistoke fluids are obtainable by further fractionation of the product.

EXAMPLE II

In accordance with the procedure of Example I, dimer and 1-decene (1:1) were reacted at 5° C. utilizing 10 mole percent phosphoric acid-modified boron trifluoride. The reaction was terminated after four hours during which time 55.6 percent conversion of the dimer was achieved. After removal of the unreacted dimer, a product having an average molecular weight of 502 with viscosity and distribution of oligomers essentially identical to the product of Example I was obtained.

EXAMPLE III

To demonstrate the versatility of the process and ability to obtain products having a different distribution of oligomers and viscosity, dimer and 1-decene were reacted (1:1 weight ratio) at 25° C. For this reaction 5 mole percent phosphoric acid was charged prior to saturation of the solution with boron trifluoride. Within less than three hours about 60 percent conversion of the dimer was obtained with approximately 95 percent conversion of the 1-decene. The reaction was terminated after four hours and the resulting product, after removal of unreacted dimer by fractional distillation, had an average molecular weight of 600 and viscosity of about 8 centistokes at 210° F. The product consisted primarily of trimer, tetramer, pentamer and hexamer (ratio of 1.8:2.6:1.8:1).

EXAMPLE IV

To demonstrate the ability to obtain useful lubricant fluids using different ratios of dimer and α-olefin, dimer and 1-decene were reacted at a 3:1 ratio using 1 mole percent phosphoric acid-modified boron trifluoride catalyst. The reaction was carried out at 25° C. in the usual manner and after four hours 60.8 percent conversion of the dimer was achieved. The product obtained from the reaction, after removal of unreacted dimer, had an average molecular weight of 536 and after hydrogenation proved to be an effective 6 centistoke lubricant fluid. This fluid can be blended with synthetic ester lubricants and formulated with conventional additives to provide useful synthetic lubricating compositions. A hydraulic fluid based on 6 centistoke synthetic hydrocarbon was formulated as follows:

75 parts 6 centistoke synthetic hydrocarbon
25 parts di-2-ethylhexyl azelate
2 parts 4,4'-methylenebis(2,6-di-t-butylphenol)
1 part tricresyl phosphate
3 parts barium dinonylnaphthalene sulfonate
0.01 part Oil Red 235

EXAMPLE V

In a manner similar to that described in Example IV, dimer and 1-decene were reacted at 25° C. in a 3:1 weight ratio using 10 mole percent of the coordinated $BF_3$ catalyst. The conversion of dimer after four hours was 59.1 percent and the resulting product had an average molecular weight of 541 and viscosity (210° F.) of about 6.4 centistokes.

EXAMPLE VI

Dimer and 1-decene were reacted at a ratio of 1:3. The reaction was carried out at 5° C. and 5 mole percent phosphoric acid-modified boron trifluoride catalyst was employed. The conversion of dimer after four hours was 56.4 percent and the resulting product had an average molecular weight of 512° and 210° F. viscosity of 5.6 centistokes.

EXAMPLE VII

Example VI was repeated except that the reaction temperature was increased to 45° C. Greater than 60 percent conversion of the dimer was realized within two hours. The reaction was terminated after four hours and yielded a product having an average molecular weight of 595 (after removal of unreacted dimer). The product was comprised primarily of trimer, tetramer, pentamer and hexamer at a ratio of 1:5.2:1.1:1.

EXAMPLE VIII

For comparative purposes and to demonstrate the inability to react the dimer using conventional alcohol-modified boron trifluoride catalysts, dimer and 1-decene (weight ratio of 1:1) were reacted in accordance with the procedure of Example I. The reaction was carried out at 10° C. using 2 mole percent 1-propanol-modified boron trifluoride as the catalyst. Less than 6 percent conversion of the dimer was obtained after two hours reaction. When the experiment was repeated using a higher reaction temperature (55° C.), the dimer conversion was still less than 6 percent.

EXAMPLE IX

To further demonstrate the unexpectedly superior results obtained by the process of this invention utilizing a phosphoric acid-modified catalyst, a series of experiments was conducted wherein dimer and 1-decene were reacted with various modified boron trifluoride catalysts, including another acid-modified $BF_3$ catalyst. All of the experiments were carried out for 4 hours at 25° C. and the initial weight ratio of dimer to decene-1 was 3:1. The catalysts employed included $BF_3$ modified with phosphoric acid, water, acetic acid, 1-propanol, acetone and ethyl ether. All catalysts were used at a 1 mole percent level, based on the dimer/decene. Samples were removed from each of the reactions at regular intervals and the distribution of oligomers present in the reaction mixture determined by gas chromatographic analysis. Results are reported in Table I.

The improved results obtained with the process of the present invention are evident from the data presented in the Table. For example, a significantly improved yield of higher oligomers is obtained with the phosphoric acid-modified $BF_3$ catalyst. Also, while 60.8 percent conversion was obtained after four hours with the phosphoric acid/$BF_3$ catalyst, the highest conversion obtained with the other catalysts was only 36.1 percent. It should also be noted that with the process of this invention, a higher dimer conversion was obtained after two hours than was possible with any of the other modified $BF_3$ catalysts after four hours.

We claim:

1. A process for converting the dimer fraction obtained from a boron trifluoride-catalyzed oligomerization of $C_{6-12}$ α-olefins to more highly useful oligomeric products which comprises reacting said dimer with an α-olefin having from 6 to 12 carbon atoms, the weight ratio of said dimer to said α-olefin being 5:1 to 1:5, at a temperature from 5° C. to 75° C. and pressure from atmospheric up to 100 psi and in the presence of 0.75 to 15 mole percent phosphoric acid-modified boron trifluoride catalyst, and separating the higher oligomers formed from unreacted dimer and α-olefin.

2. The process of claim 1 wherein the dimer is derived from an α-olefin having from 8 to 10 carbon atoms.

3. The process of claim 2 wherein the weight ratio of dimer to α-olefin ranges from 3:1 to 1:3 and the α-olefin contains from 8 to 10 carbon atoms.

4. The process of claim 3 wherein the temperature is 5° C. to 45° C. and pressure ranges from atmospheric up to 10 psi.

5. The process of claim 4 wherein the phosphoric acid-modified boron trifluoride catalyst is present in an amount from 1 to 10 mole percent.

6. The process of claim 5 wherein the higher oligomers formed are hydrogenated prior to separation from the unreacted dimer and α-olefin.

7. The process of claim 2 wherein the dimer has a 210° F. viscosity in the range 1.7 to 2.2 centistokes and contains less than about 5 percent by weight higher oligomers.

* * * * *

TABLE I

| TIME (MINS.) | WEIGHT PERCENT | PHOSPHORIC ACID | WATER | ACETIC ACID | 1-PROPANOL | ACETONE | ETHYL ETHER |
|---|---|---|---|---|---|---|---|
| 0 | 1-decene | 25 | 25 | 25 | 25 | 25 | 25 |
|   | dimer | 75 | 75 | 75 | 75 | 75 | 75 |
| 60 | 1-decene | 2.3 | 7.8 | 6.6 | 6.5 | 13.9 | 8.0 |
|   | dimer | 70.8 | 70.4 | 70.2 | 63.7 | 70.6 | 64.6 |
|   | higher oligomers | 26.9 | 21.8 | 22.6 | 29.2 | 14.8 | 26.6 |
| 120 | 1-decene | 1.0 | 1.4 | 3.5 | 2.8 | 6.2 | 3.1 |
|   | dimer | 46.2 | 64.0 | 67.2 | 59.5 | 68.0 | 59.0 |
|   | higher oligomers | 52.0 | 34.5 | 28.7 | 37.1 | 24.7 | 36.9 |
| 180 | 1-decene | 1.0 | 1.3 | 3.0 | 2.1 | 3.2 | 2.4 |
|   | dimer | 34.0 | 54.4 | 61.8 | 55.8 | 64.0 | 58.0 |
|   | higher oligomers | 63.8 | 44.1 | 34.2 | 41.5 | 31.8 | 38.9 |
| 240 | 1-decene | 1.0 | 1.2 | 2.4 | 1.6 | 2.2 | 1.9 |
|   | dimer | 29.4 | 47.9 | 55.3 | 51.2 | 59.3 | 51.9 |
|   | higher oligomers | 68.5 | 50.9 | 39.8 | 46.1 | 37.4 | 45.2 |